United States Patent [19]

Menken et al.

[11] 4,151,513

[45] Apr. 24, 1979

[54] APPARATUS FOR SENSING AND TRANSMITTING A PACEMAKER'S STIMULATING PULSE

[75] Inventors: John D. Menken, St. Paul; Brian A. Brastad, Wayzata; Thomas C. Barthel, Becker, all of Minn.

[73] Assignee: Medtronic, Inc., Minneapolis, Minn.

[21] Appl. No.: 555,897

[22] Filed: Mar. 6, 1975

[51] Int. Cl.² .................. G08C 19/22; A61B 5/04
[52] U.S. Cl. ...................... 340/206; 128/2.1 A; 128/2.06 R; 128/419 PT; 179/2 DP; 340/180
[58] Field of Search ................ 340/206, 180; 128/2.1 A, 419 PT, 2.05 R, 2.06 R; 179/2 DP; 307/225 R

[56] References Cited

U.S. PATENT DOCUMENTS

| | | | |
|---|---|---|---|
| 3,657,658 | 4/1972 | Kubo | 307/225 R |
| 3,769,965 | 11/1973 | Raddi et al. | 128/419 PT |
| 3,780,727 | 12/1973 | King | 128/419 PT |
| 3,871,363 | 3/1975 | Day | 128/419 PT |
| 3,872,252 | 3/1975 | Malchman et al. | 128/419 PT |
| 3,885,552 | 5/1975 | Kennedy | 128/419 PT |
| 3,920,005 | 11/1975 | Gombrich et al. | 128/419 PT |
| 3,923,041 | 12/1975 | Stasz | 128/419 PT |

OTHER PUBLICATIONS

Furman, "Medical Instrumentation", May–Aug. 1973, pp. 196–202.

*Primary Examiner*—John W. Caldwell, Sr.
*Assistant Examiner*—James J. Groody
*Attorney, Agent, or Firm*—R. Lewis Gable; Harry W. Barron

[57] ABSTRACT

Apparatus is disclosed for sensing and transmitting the stimulating pulse of an implanted pacemaker over readily available, low-bandwidth transmission media to a remote receiver capable of measuring the pulse width to provide an indication of the condition of the pacemaker energy source, e.g. a battery. In particular, the sensing and transmitting apparatus detects the electrical activity, e.g. the EKG, of a patient through attached electrodes and modulates a carrier or tone of a suitable frequency to be transmitted over the low-bandwidth transmission medium to the receiver, along with a pulse signal multiplied by a selected, fixed factor dependent upon the carrier frequency of the signal and the other information to be transmitted to the receiver. Illustratively, a factor in the range of 30–50 is selected where it is desired to transmit the pulse width of the pacemaker stimulating pulse along with an EKG, to a receiver to be displayed in a manner to permit evaluation of the EKG and of the width of the stimulating pulse. Typically, the patient in which the pacemaker is implanted has a transmitter for transmitting the aforementioned data to a receiver located in the doctor's office, clinic or hospital, whereby a regular check of the pacemaker's energy source may be made by the patient's doctor.

2 Claims, 21 Drawing Figures

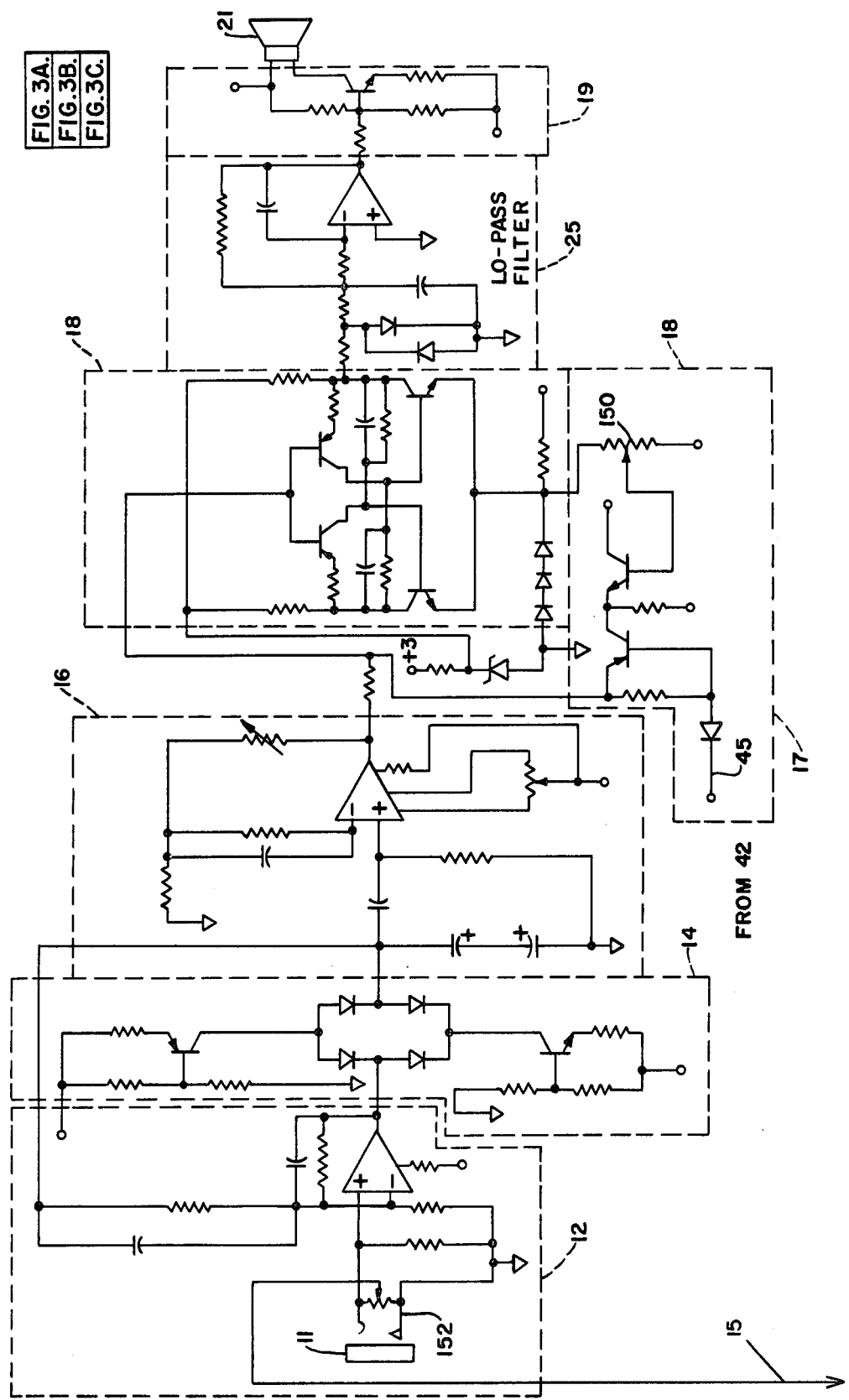

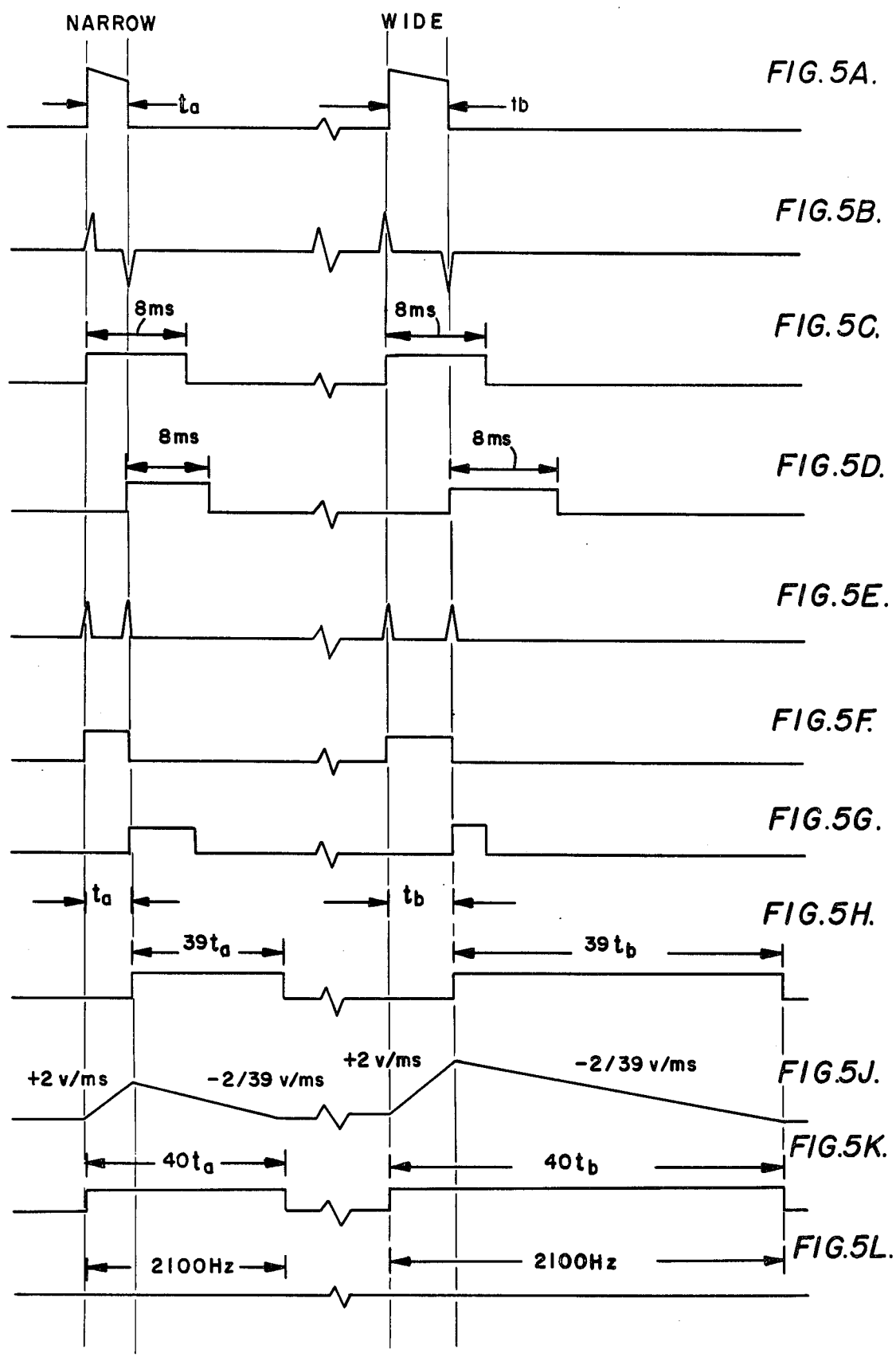

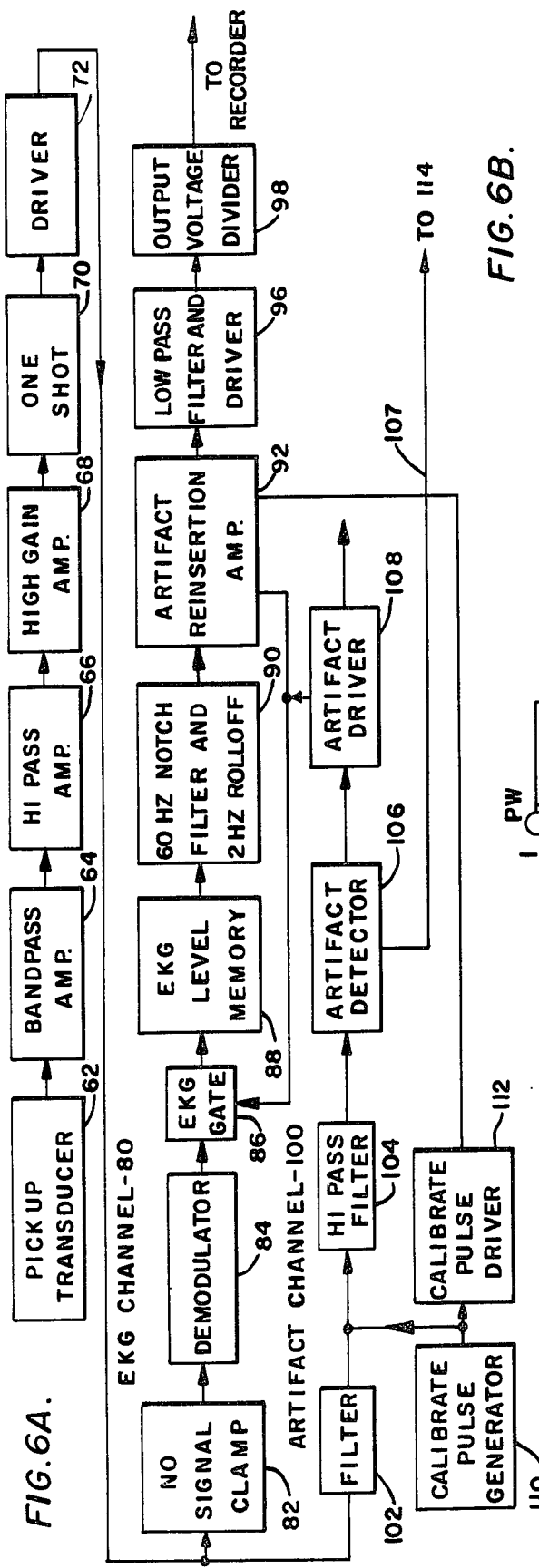
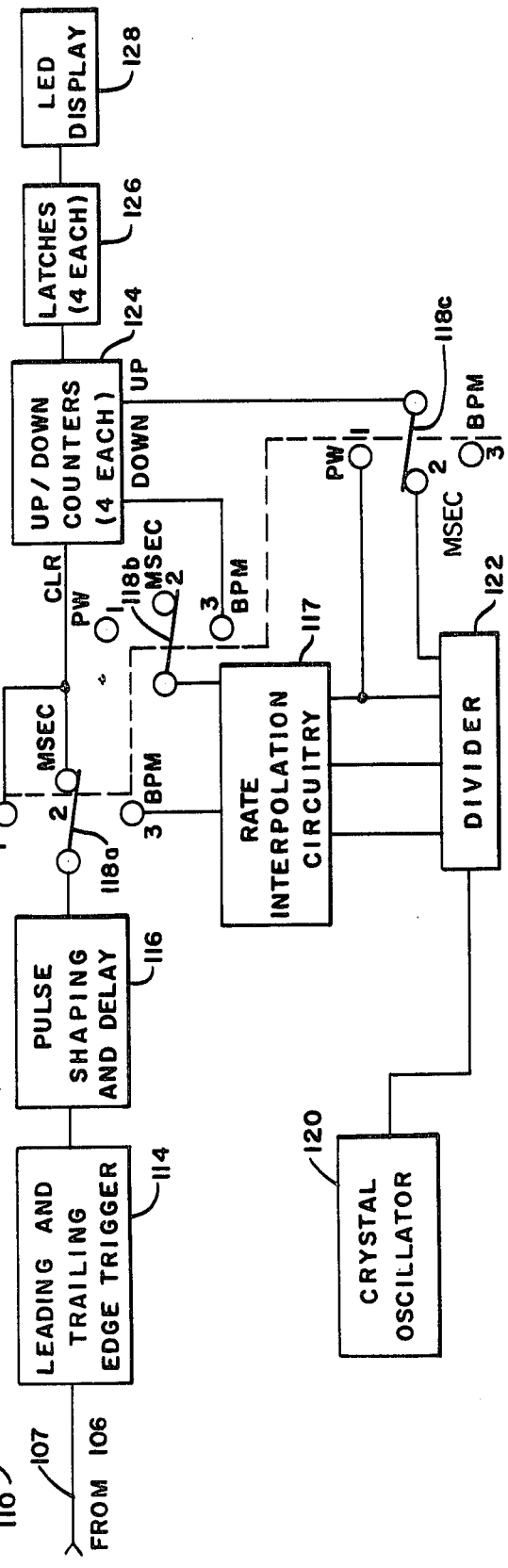
FIG. 6A.
FIG. 6B.

APPARATUS FOR SENSING AND TRANSMITTING A PACEMAKER'S STIMULATING PULSE

CROSS-REFERENCE TO RELATED APPLICATION

Reference is made to the related application Ser. No. 555,896, filed concurrently herewith now U.S. Pat. No. 3,986,496 in the name of Brian A. Brastad, entitled "Apparatus for Sensing and Transmitting a Pacemaker's Stimulating Pulse" and assigned to the assignee of this invention.

BACKGROUND OF THE INVENTION

1. Field of the Invention

This invention relates to apparatus for modulating a carrier with information to be transmitted over a relatively low-bandwidth transmission medium in a manner to permit its detection at a receiver and in particular to such apparatus adapted to transmit data indicative of the width of a pacemaker stimulating pulse to a remote location, whereby the pulse width may be accurately determined to provide an indication of the pacemaker's energy source, e.g. a battery.

2. Description of the Prior Art

Heart pacemakers such as that described in U.S. Pat. No. 3,057,356, issued in the name of Wilson Greatbatch and assigned to the assignee of this invention, are known for providing electrical stimulus to the heart whereby it is contracted at a desired rate in the order of 72 beats per minute. A heart pacemaker is capable of being implanted in the human body and operative in such an environment for relatively long periods of time, to provide cardiac stimulation at relatively low power levels by utilizing a small, completely implanted, transistorized, battery-operated pacemaker connected via flexible electrode wires directly to the myocardium or heart muscle. The electrical stimulation by this pacemaker is provided at a relatively fixed rate.

Such cardiac pacers of the implantable variety have found wire acceptance for patients suffering from complete heart block. As a result, the use of these pacers has increased the life expectancy of those patients with implants, from a 50% probability of one (1) year to nearly the life expectancy of physically-comparable humans not suffering from the same heart disorder.

Typically, such cardiac pacers are encapsulated in a substance substantially inert to body fluids, and are implanted within the patient's body by a surgical procedure wherein an incision is made in the chest beneath the patient's skin and above the pectoral muscles or in the abdominal region, and a pacemaker is implanted therein. Due to the inconvenience, expense and relative risk to the patient's health, it is highly desired to extend the life of the power source or battery, whereby the number of such surgical procedures is limited. The resultant problem for the attendant doctor is to determine when the batteries should be replaced, keeping in mind the relative risk or probability of premature pacer failure due to battery depletion.

A number of solutions to this problem have been proposed, one being replacement at predetermined intervals, thus accepting an empirically determined risk or failure of the pacemaker batteries. Another proposed solution is to establish pacer "clinics" where photographic analysis techniques are used to detect imminent failure. These solutions are not entirely satisfactory for detecting, simply and positively, a degradation of pacer system performance. The risk of undetected premature failure associated with periodic replacement intervals at predetermined intervals is obviously undesirable. Photo-analysis techniques are complicated, not positive in detection and require that the patient be physically present in the physician's office. Further, such techniques are not readily available to physician and patient on short notice, but rather, as mentioned previously, would be available only at special clinics.

In U.S. Pat. No. 3,618,615, assigned to the assignee of this invention, there is disclosed an artificial cardiac pacemaker for generating at regular intervals a train of stimulating pulses, one of which is of significantly lower energy than the other pulses. If the heart responds to the reduced energy stimulating pulse, an adequate safety factor remains, but if the heart does not respond, e.g. no beat is detected in response to the lower energy or test pulse, marginal operation and possible imminent failure is ascertained.

Another method of ascertaining the pending failure of a pacemaker energy source is described in U.S. Pat. No. 3,713,449, assigned to the assignee of this invention, describing an artificial pacemaker including means for varying selectively the pulse width of its stimulating pulse. Control of the pulse width is made preferably by a mechanism external of the body by an attending physician. By such mechanism, the physician varies the pulse width of the implanted pacemaker until capture is lost. As the physician has previously measured the pulse width at the time of pacemaker implant, the pulse width at a subsequent time may be varied until capture is lost, whereby the state of the battery can be determined with respect to its replacement.

In an alternative approach to the problem of accurately determining battery depletion, there are artificial pacemakers such as described in U.S. Pat. No. 3,842,844 having a battery or cell depletion indicator that increases the pulse width of the output signal as their batteries deplete, i.e. their voltage amplitude decreases. Further, as the power source or battery depletes, the pulse repetition rate of such artificial cardiac pacemakers also decreases. For example, at the time of implantation, an artificial cardiac pacemaker may produce stimulating pulses at 70 beats per minute (BPM), plus or minus two beats, with a pulse width in the order of 0.5 msec. After a period of service illustratively in the order of 2–4 years, the BPM changes in the order of 5%–10%, i.e. a decrease of 5–7 beats from the original BPM, and the pulse width may increase to a value in the order of 1 msec. Dependent upon the known histories of such batteries, such a change in the BPM as well as a change in pulse width indicates that one of a plurality (e.g. 4 or 5) cells has failed, and that it is time to replace the batteries within the implanted pacemaker to assure continued heart stimulation of a sufficient level.

Pulse width increase is desired in order that as the amplitude of the voltage provided from the pacemaker battery decreases, the total energy in the stimulating pulse remains substantially constant. It is understood that the voltage level of the pacemaker battery may decrease below a lever at which the heart may not respond regardless of the pulse width. Further, as the pulse width increases to compensate for decreases in the voltage level, the current drain upon the battery increases, thereby increasing the rate of battery depletion.

As indicated above, one of the disadvantages of the prior art schemes with regard to determining pacemaker energy source depletion, is that it requires the patient to be physically present in the doctor's office, hospital or clinic. At the present time, there are systems such as described in U.S. Pat. No. 3,923,041, assigned to the assignee of this invention for sensing via electrodes attached to the patient's body the electrical activity of the heart including the stimulating pulses applied thereto from an artificial cardiac pacemaker and for transmitting such signals over readily available transmission media such as the telephone lines, to a remote station in the doctor's office, hospital or clinic, for example, where a trained person, such as the physician or his aide, may conveniently monitor the heart activity. In this manner, regular checkups of the patient's heart may be made without requiring the patient to travel to the hospital, clinic or doctor's office.

In FIG. 4 of the drawings, there is shown a typical graph of the electrical activity of a patient's heart which is stimulated by pulses derived from an artificial cardiac pacemaker. The heart activity or electrocardiogram (EKG) of the patient is indicated in FIG. 4 by the letter "B", whereas the stimulating pulse is identified by the letter "A", whose pulse width is indicated with the letters "PW". Noting that the threshold for stimulation of the heart varies from patient to patient, the minimum pulse width of the stimulating pulse is in the order of 100μsec and its minimum voltage amplitude is in the order of 0.5V. Typically, the amplitude of the stimulating pulse would be in the order of 6V.

In view of the narrow bandwidth of telephone transmission lines, low carrier frequencies in the order of 1500Hz are used to transmit such signals. As a result, it is not possible to transmit with accuracy, the width of the pacemaker stimulating pulse. Typically, the pulse width of an artificial cardiac pacemaker may vary from 0.15 msec to about 3 msec. A significant portion of a pulse of such narrow width is lost when superimposed upon a low carrier frequency. Thus, though it would be possible to transmit directly such a pulse to a remote station, the detected pulse width would not be reproduced with sufficient accuracy to indicate with the desired precision the state or life of the pacemaker energy source.

SUMMARY OF THE INVENTION

It is therefore an object of this invention to provide an accurate indication of the state of an artificial pacemaker power source, without requiring a patient with an implanted pacemaker to be present in the doctor's office, clinic or hospital.

It is a further object of this invention to provide apparatus for transmitting with significant accuracy the artificial pacemaker stimulating pulse as detected from the patient, whereby its pulse width may be accurately determined and displayed at a remote station.

In accordance with these and other objects, there is disclosed apparatus for detecting through electrodes attached to the patient's body, the electrical activity of the patient's heart and the stimulating pulses applied thereto by an implanted cardiac pacemaker, and for transmitting these signals upon relatively narrow bandwidth transmission media such as telephone lines, to be received and suitably displayed together in a manner such that the width of the artificial pacemaker stimulating pulse may be accurately determined. In particular, the stimulating pulse is detected and amplified and then subsequently multiplied by a factor selected in view of the relatively low carrier frequency to ensure that upon subsequent detection and display, other cardiac electrical activity is not obscured. The multiplied pulse is imposed upon the carrier frequency without loss of sufficient accuracy as to its width.

In the complete system of this invention, the multiplied signal is superimposed upon the detected other activity of the heart, e.g. the patient's electrocardiogram (EKG), and is converted by a suitable transducer to a sound directed into the mouthpiece of a telephone, whereby the heart data may be transmitted over telephone lines to a remote station in the doctor's office, hospital or clinic, for example. At the remote station, a receiver coupled to a telephone earpiece converts the received sound to electrical signals to be processed, i.e. to separate the multiplied stimulating pulse from the remainder of the transmitted heart activity signal and to measure its width. The measured pulse width data is displayed upon a suitable display, e.g. a light-emitting diode display, whereby the patient's doctor may accurately predict the life expectancy of the pacemaker's power source.

BRIEF DESCRIPTION OF THE DRAWINGS

These and other objects and advantages of the present invention will become more apparent by referring to the following detailed description and accompanying drawings, in which:

FIGS. 3A, 3B and 3C are detailed, schematic drawings of the transmitter more generally shown in FIGS. 1A and 2, and are inter-related as shown in FIG. 3;

FIGS. 5A to 5L show the various signals as provided in the block diagram of the transmitter of FIG. 2; and FIGS. 6A and 6B show a simplified block diagram of the receiver as generally shown in FIG. 1B.

DESCRIPTION OF THE PREFERRED EMBODIMENTS

Figure 1A:
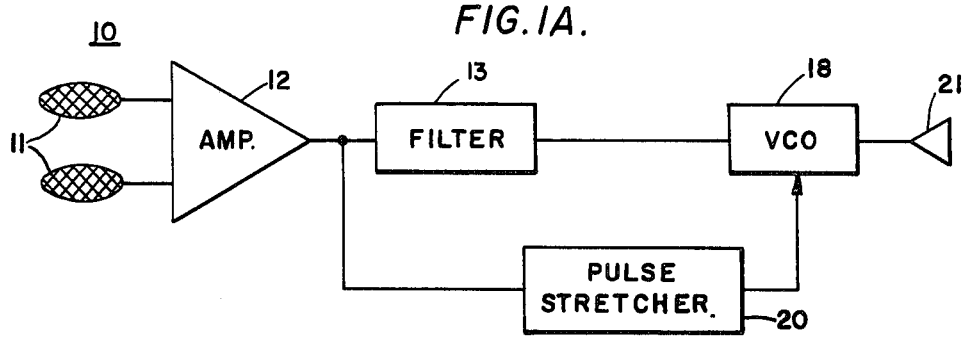
FIG. 1A is a simplified, block diagram of the transmitter in accordance with the teachings of this invention.
Figure 1B:
FIG. 1B is a simplified diagram showing the transmitter as shown in FIG. 1A for transmitting the electrical activity of the patient's heart along a transmission medium to a receiver.

Referring now to the drawings and in particular to FIG. 1B, there is shown a simplified diagram illustrating the relationship of a transmitter 10 in accordance with the teachings of this invention for detecting and transmitting the electrical activity of the patient's heart, e.g. the patient's electrocardiogram (EKG) upon which has been superimposed the detected stimulating pulse multiplied by a selected factor, across a relatively low bandwidth transmission medium 50 to be received by a receiver 60, which operates to separate the multiplied stimulating pulse and to display it with significant accuracy, whereby the attending physician can determine accurately the width of the stimulating pulse and the state of the pacemaker's energy source. It is evident that the transmitter 10 may be a relatively portable unit that is adapted to be coupled to a telephone set, whereby the desired signals are transmitted over the telephone lines or transmission medium 50. At the end of the transmission medium 50, the receiver 60 is adapted to be coupled to another telephone set, whereby the transmitted signal may be converted to electrical signals within the receiver 60 to be processed and displayed as to be described in more detail.

In FIG. 1A, there is shown a simplified schematic of the transmitter 10, shown in block form in FIG. 1B. In particular, a pair of electrodes 11 is attached to the patient, as upon the inside of his forearms, whereby the electrical activity of the patient's heart and the stimulating pulse as generated and applied to the patient by the implanted artificial pacemaker, are detected and applied to an amplifier 12. the detected signal is amplified by the amplifier 12 before being applied to the EKG channel comprised of a filter 13 and a voltage-controlled oscillator 18. The filter 13 serves to block the pacemaker stimulating pulse from the EKG channel. Further, the amplified signal is also applied to a pulse stretcher 20 whereby the stimulating pulse is detected and amplified to be subsequently stretched by a fixed factor, dependent upon the carrier signal to be transmitted along the transmission medium 50 to a display, e.g. a strip recorder, within the receiver 60, whereby the pulse width as displayed thereon does not mask other information of interest to the patient's doctor. Illustratively, the factor is selected to be within the range of 30–50 with a preferred value being in the order of 40. By selecting a multiplication factor in the noted range, the superimposed, multiplied pulse is of sufficient duration with respect to the frequency of the carrier signal, that no significant amount of the width of the stimulating pulse is lost. At the same time, even with a factor of 50, a pulse of normal width, e.g. .0 msec, as received and displayed by the receiver 60 does not unduly mask the other information as displayed at the remote station. When an abnormal pulse of extended width, e.g. 3 msec, is detected and displayed by the receiver 60, the stretched pulse may obscure other data of interest. However, the display of such a wide pulse is desired in that it provides a warning that the pacemaker battery may be nearly depleted.

Figure 2:
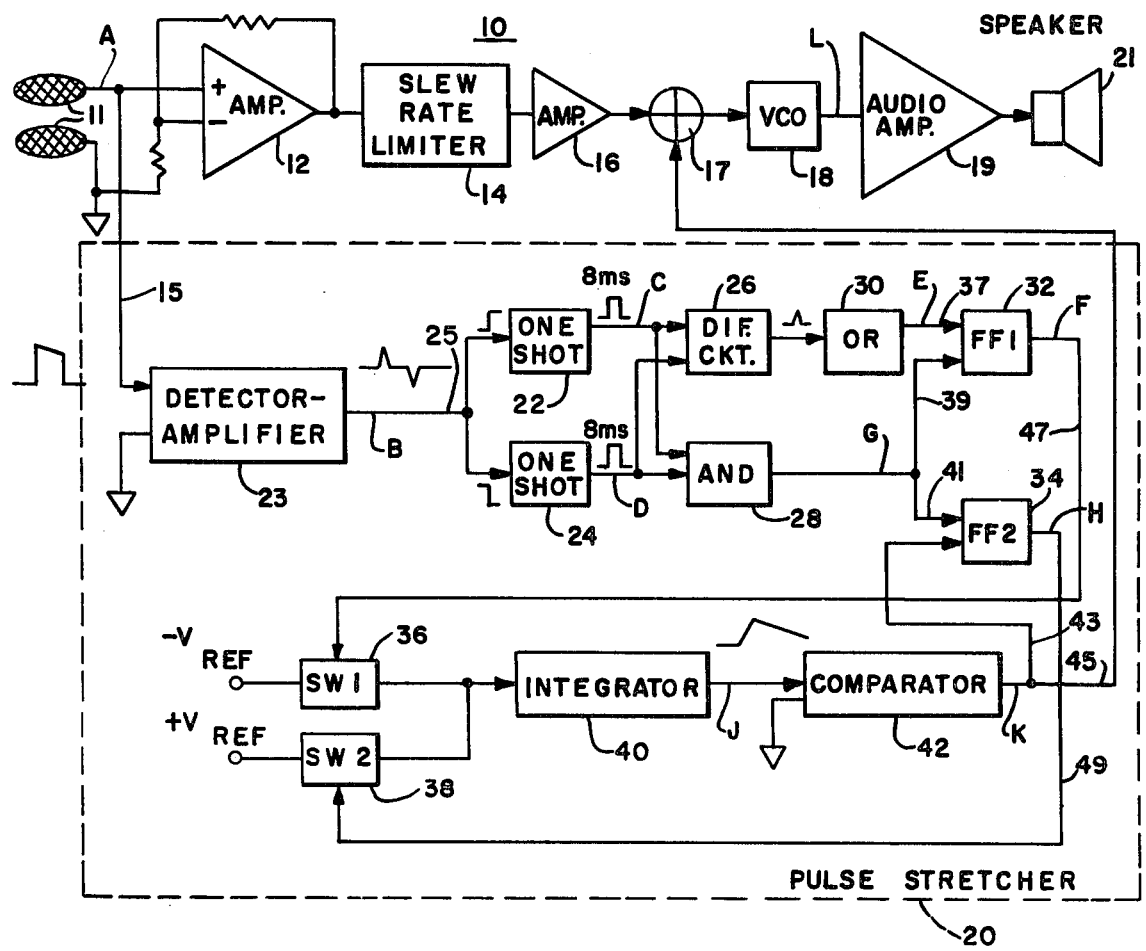
FIG. 2 is a more detailed, block diagram of the transmitter as generally shown in FIG. 1A.

In FIG. 2, there is shown a more detailed block diagram of the transmitter 10 generally shown in FIGS. 1A and 1B. In particular, the electrical activity of the heart with the stimulating pulse imposed thereon is sensed by the electrodes 11 and applied thereby to an EKG channel comprised of the amplifier 12, a slew rate limiter 14 and an amplifier 16. Likewise, the detected activity is applied by conductor 15 to a pulse stretcher or multiplier 20, comprised of a detector-amplifier 23 which serves to differentiate and amplify the pacemaker stimulating pulse, shown in FIG. 5A, to provide first and second spikes for each stimulating pulse width received. As illustrated in FIG. 5B, the leading edge of the detected stimulating pulse causes detector-amplifier 23 to generate a positive-going pulse, whereas the trailing edge of the stimulating pulse causes detector-amplifier 23 to generate a negative-going pulse. As shown in FIG. 2, the series of positive- and negative-going pulses are applied by a conductor 25 to first and second one-shot multipliers 22 and 24. In FIG. 2, letters "A", "B", "C", etc. are used to denote the signals appearing at various points in the circuit and correspond to these signals' waveforms as shown in FIGS. 5A to 5L. For example, the series of positive- and negative-going pulses as shown in FIG. 5B are applied to both of the one-shot multipliers 22 and 24. The positive-going pulse corresponding to the leading edge of the stimulating pulse triggers the one-shot multiplier 22 to generate a pulse-like signal of fixed duration, e.g. 8 msec, as shown in FIG. 5C, whereas the negative-going pulse corresponding to the trailing edge of the stimulating pulse causes one-shot multiplier 24 to generate a pulse of fixed duration, e.g. 8 msec. As shown by a comparison of FIGS. 5A, 5C and 5D, the leading edge of the fixed duration pulses as derived from the one-shot multipliers 22 and 24 are spaced from each other by a period corresponding to the width of the stimulating pulse.

As shown in FIG. 2, the fixed pulses derived from one-shot multipliers 22 and 24 are both applied to a differentiating circuit 26, whose output is coupled through an OR circuit 30 to apply an output as shown in FIG. 5E comprised of a series of positive-going pulses to the set terminal of a first flip-flop 32. The differentiating circuit 26 differentiates the pulse-like signals, providing spikes corresponding to the leading edge of the fixed pulse width signals, thereby rendering the OR circuit 30 relatively insensitive to changing DC levels but responsive to the rising, spiked signals. The output of the OR circuit 30, as shown in FIG. 5E, comprises a series of positive-going pulses spaced apart from each other a distance corresponding to the pulse width of the stimulating pulse and serve to set the first flip-flop 32, whose output goes high, as shown in FIG. 5F, upon being set.

Further, the fixed pulse width signals derived from the one-shot multipliers 22 and 24 are both applied to an AND circuit, which upon coincidence of its input signals, applies an output signal as shown in FIG. 5G, to reset the first flip-flop 32 and to set a second flip-flop 34. As shown in FIG. 2, the output of the AND circuit 28 is applied to the reset terminal of the first flip-flop 32 along the conductor 39, and to the second flip-flop 34 along conductor 41. As can be seen from a comparison of FIGS. 5A, 5D and 5G, an output from the one-shot multiplier 24 corresponds to the trailing edge of the stimulating pulse and serves to set the AND circuit 28, whereby the first flip-flop 32 is reset. Thus, the output of the first flip-flop 32 lasts for a period corresponding to the width of the detected stimulator pulse.

Further, the AND circuit 28 serves to distinguish stimulator pulses from other, extraneous signals that may be imposed upon the electrodes 11, requiring coincidence of the fixed pulse width signals before resetting the first flip-flop 32. In particular, the fixed pulse width of the signals derived from the one-shot multipliers 22 and 24 is set illustratively at 8 msec, and the pulse width of a real stimulating pulse is typically less than 8 msec. Thus, if an extraneous signal having a pulse width greater than 8 msec is detected, a coincidence condition will not be sensed by AND circuit 28 to reset flip-flop 32 and a stretched pulse will not be transmitted by the transmitter 10.

Further, the output of the one-shot multiplier 24 is applied by way of the differentiating circuit 26 and the OR circuit 30 to tend to set the first flip-flop 32. However, the differentiator circuit 26 responds to the leading edge of the output of the one-shot multiplier 24 to provide a sharp pulse-like signal. By comparison, the reset pulse derived from AND circuit 28 is of relatively long duration, i.e. the total overlap between the outputs of the one-shot multipliers 22 and 24, whereby the tendency to set flip-flop 32 is overriden and in fact, the first flip-flop 32 is reset.

As shown in FIG. 2, the output derived from the first flip-flop 32 is applied by a conductor 47 to control a first switch 36, whereby when the output of the flip-flop 32 is high, the first switch 36 applies a negative reference signal −Vref to an integrator 40, tending to integrate the reference signal in a positive direction, as shown in FIG. 5J. As explained above, the first flip-flop 32 is set and therefore the first switch 36 is turned on for a first period of time corresponding to the width of the stimulating pulse to be stretched or multiplied. Thus, in the first period of time, the integrator 40 integrates the negative reference voltage −Vref at a first, relatively high rate whereby the amplitude of the integrator 40 at the termination of the first period is proportional to the width of the stimulating pulse. The first period is terminated upon the first flip-flop 32 being reset to turn off the first switch 36, at which time the second flip-flop 34 is set to provide a high output as shown in FIG. 5H to a second switch 38, which is turned on to apply a positive reference potential +Vref to the integrator 40. In response to the positive ref potential, the integrator 40 integrates in a negative-going direction at a second, significantly slower rate than the first rate for a second period of time.

As shown in FIG. 2, the output of the integrator 40 is applied to a comparator 42, which compares the output of integrator 40 with a reference level, illustratively set at ground potential. Thus, when the output of the integrator 40 is in excess of the reference or ground potential, the output from the comparator 42 goes high, as seen in FIG. 5K. The output of the comparator 42 is applied by a conductor 43 to reset the second flip-flop 34. In particular, as shown in FIGS. 5K and 5H, the trailing edge of the output of the comparator 42 serves to reset the second flip-flop 34, whereby the second switch 38 is rendered non-conductive and the integrator 40 ceases to integrate the +Vref signal, as shown in FIG. 5J. As indicated in FIG. 5J, the integrator 40 integrates during the first period the negative-going reference potential −Vref at a first, relatively high rate, e.g. +2v/ms and integrates during the second period the positive reference potential +Vref at a second, relatively slow rate, e.g. −2v/39ms. Thus, if the width of the stimulating pulse is "ta", as shown in FIG. 5A, the sum of the first and second periods corresponds to 40 "ta", thus providing a means for multiplying the stimulating pulse for a preselected factor, e.g. 40. It is understood that the integrating rates for the first and second periods may be set at other values, whereby the multiplication factor may be set in the range of 30–50. Thus, the output of the comparator 42 representing the multiplied stimulating pulse, as shown in FIG. 5K, goes high for a period corresponding to 40ta, and is further applied to a summing point 17.

Turning our attention back to the EKG channel as shown in FIG. 2, the detected electrical activity of the patient's heart along with the pacemaker, stimulating pulse superimposed thereon, is applied to the amplifier 12 which amplifies the input signal by a fixed gain, e.g. 11, to provide the amplified output to a slew rate limiter 14, which operates to limit the amplitude of signals passing therethrough, whereby the stimulating pulses are substantially eliminated from the EKG channel. In particular, the slew rate limiter 14 limits the rate of increase of the input signals to a value, e.g. −100v/sec, whereby the EKG signals varying in amplitude in the range of 1 to 5mV and of a frequency in the range of 0 to 50 or 70 Hz pass thereby and the stimulating pulses are effectively blocked. The limited signals are further amplified by an amplifier 16 to be applied with the multiplied stimulating pulse inserted at summing point 17 to a voltage-controlled oscillator (VCO) 18. The VCO 18 is responsive to the amplitude of the input signal derived from the summing point 17 to provide an output of a frequency proportional to its voltage level. As a result, the amplified signal derived from the amplifier 16 indicative of the EKG activity controls the voltage-controlled oscillator to provide an output whose frequency varies about a nominal or center frequency in the order of 1500 Hz. As shown in FIGS. 5K and 5L, the high output of the comparator circuit 42 increases the center frequency of the VCO 18 to about 2100 Hz for a period corresponding to that of the stretched pulse. The VCO output is applied to be amplified by an audio amplifier 19, whereby a transducer such as an audio speaker 21 produces a carrier signal in the audio range, capable of being transmitted via a relatively low bandwidth transmission line such as a telephone line 50. Though not shown, it is understood that the speaker 21 would be disposed adjacent or coupled to a telephone mouthpiece, whereby the tone is converted to electrical signals to be transmitted via the telephone lines.

As explained above, the output of the comparator 42 is applied by a conductor 45 to the summing point 17. When the output of the comparator 42 is high as shown in FIG. 5J, corresponding to a period equal to the width of the stimulating pulse multiplied by a fixed factor, e.g. 40, the input of the VCO 18 is clamped by the comparator output, substantially ignoring the output of the amplifier 16, whereby the output of the VCO 18 is driven to a frequency dependent primarily upon the comparator output, e.g. a frequency of 2100 Hz, as illustrated in FIG. 5L. As a result, the VCO 18 applies a signal of a frequency of 2100 Hz to the speaker 21, whereby a corresponding electrical signal is transmitted via the telephone lines 50 to be detected and processed by the receiver 60 to provide an indication as upon a digital, LED display of the period of the 2100 Hz tone burst, corresponding to the pulse width of the stimulating pulse.

Figure 3B:
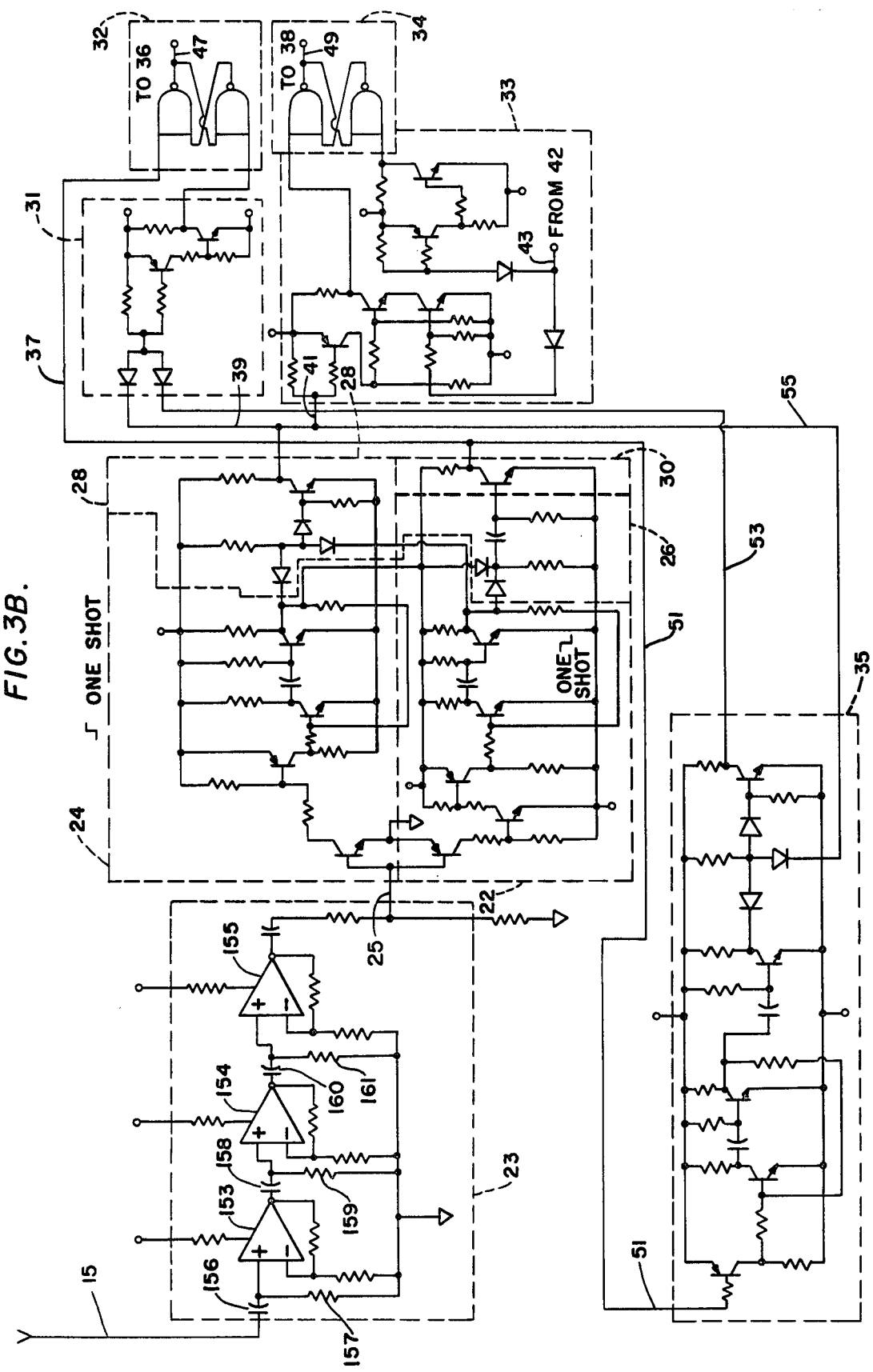
Figure 3C:
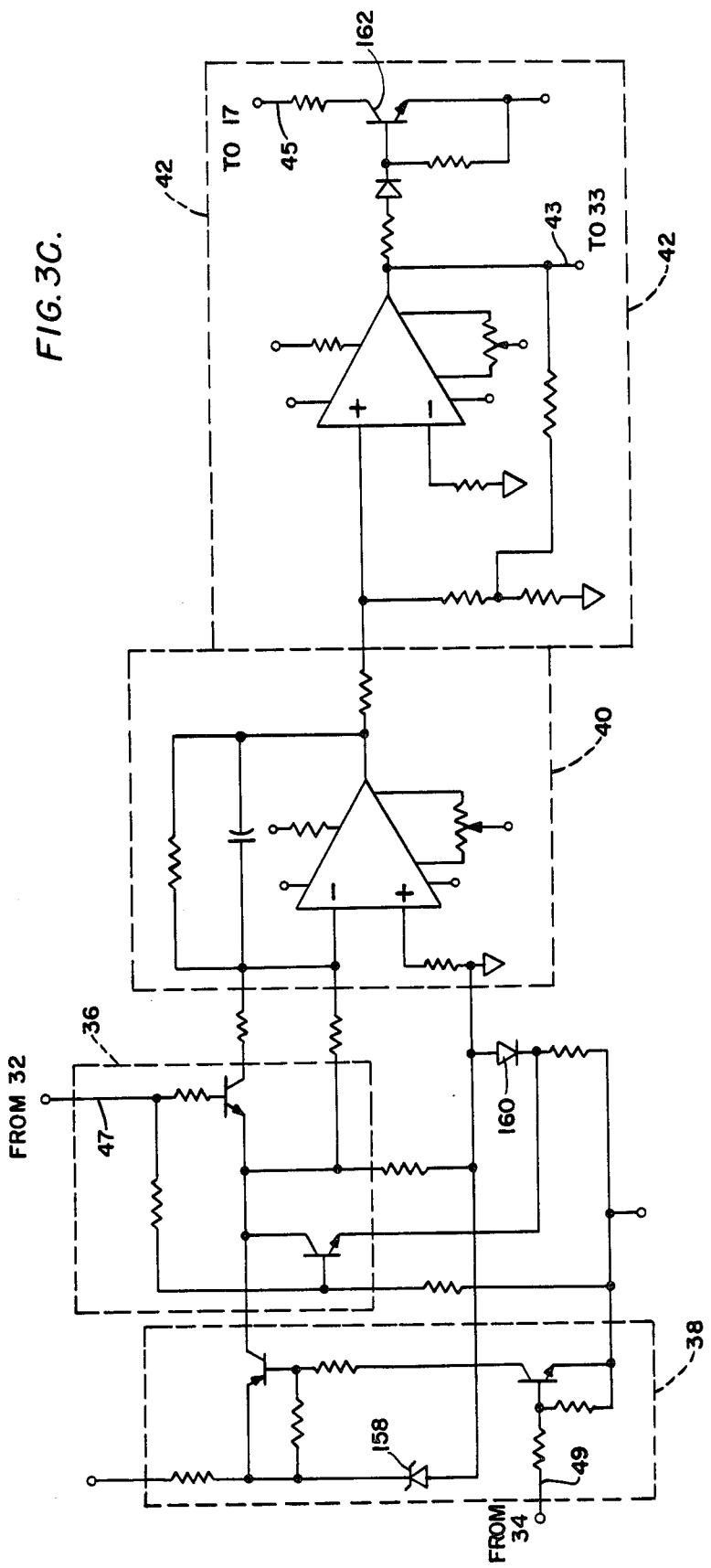

In FIGS. 3A, 3B and 3C, there is shown a detailed, schematic diagram of the circuit elements making up the transmitter as shown in block form in FIG. 2, wherein the elements composing each of the blocks shown in FIG. 2 are outlined in dotted line and are identified with corresponding numbers. In particular, the electrical activity of the patient's heart including the superimposed stimulating signals are applied by electrodes 11 to the amplifier 12, whose output is coupled to the EKG channel comprised of the slew rate limiter 14, the amplifier 16, the summing point 17 and the VCO 18. As indicated in FIG. 3A, the summing point or circuit 17 includes a variable resistor 150, whereby the output of the comparator 42 shown in FIG. 3B and applied by a conductor 45 may be adjusted to derive an output from the VCO 18 of selected frequency. In turn, the output of the VCO 18 is passed through a low-pass filter 25 (not shown in FIG. 2) before being amplified by the audio amplifier 19 to energize the speaker 21. The low-pass filter 25 removes extraneous signals to render the energizing signal applied to the speaker 21 more sinusoidal, thus making the signal detected at the receiver 60 more readable, as upon an oscilloscope.

As shown in detail in FIG. 3B, the sensed electrical activity of the patient's heart along with the detected stimulating pulse applied thereto is also applied by the conductor 15 to the detector-amplifier 23. In particular, the signal is derived from a sensitivity adjustment potentiometer 152 (see FIG. 3A) and applied by the conductor 15 to be differentiated by a first differentiating circuit comprised of capacitor 156 and resistor 157, before being amplified by amplifier 153. Subsequently, the signal is differentiated by a differentiating circuit comprised of capacitor 158 and resistor 159 before being amplified by amplifier 154. In turn, the output of amplifier 154 is differentiated by a differentiating circuit comprised of capacitor 160 and resistor 161, before being amplified by amplifier 155. The output of the amplifier-detector 23 as derived from amplifier 155, is sufficiently amplified and shaped to precisely trigger the control circuitry of the pulse stretcher 20, now to be described in detail. In particular, the amplifier output is applied by the conductor 25 to each of the one-shot multipliers 22 and 24. The output of the one-shot multiplier 22 is applied through the RC differentiating circuit 26 to the OR circuit 30 whose output is applied by conductor 37 to set the first flip-flop 32. The outputs of the one-shot multipliers 22 and 24 both are applied to the AND circuit 28 comprised of three diodes and a transistor, whose output is applied by conductor 39 to an OR circuit 31, which resets the first flip-flop 32. Further, the output of the OR circuit 30 is also applied along conductor 51 to a trailing edge monitor circuit 35, to initiate the timing of the predetermined period, e.g. 5 msec. The output of the AND circuit 28 indicative of the presence of the trailing edge is applied along conductor 55 to inhibit the trailing edge monitor circuit 35. In the absence of a signal from the AND circuit 28, the trailing edge monitor circuit 35 generates a reset signal to be applied along conductors 53 to the OR circuit 31, whereby flip-flop 32 is reset. Thus, in the presence of extraneous noise where no defined trailing edge is detected, the trailing edge monitor 35 serves through its associated OR circuit 31 to reset the flip-flop 32 in preparation for receiving and processing the next detected stimulating pulse.

In FIG. 3C, there is shown the detailed circuitry of the switches 36, 38, the integrator 40 and the comparator 42. In particular, the positive reference voltage is developed across a zener diode 158 to which is applied a voltage, e.g. 9V, developed by an unregulated power source. In a similar manner, the negative reference voltage −Vref is developed across a light-emitting diode 160. Dependent upon which of the flip-flops 32 or 34 is energized, one of the switches 36 or 38 is actuated to apply its reference voltage to the integrator 40, whose output in turn is applied to the comparator 42. As explained above, the output of the comparator as derived from the collector of transistor 162 is applied by conductor 45 to the summing point 17 as shown in FIG. 3A.

In FIGS. 6A and 6B, there is shown a block diagram of the receiver 60, generally shown in FIG. 1A. The receiver 60 is designed to decode and display a frequency-modulated carrier signal as transmitted over the transmission line 50 and converted to an audio sound by an ordinary telephone mouthpiece. The receiver 60 displays the transmitted EKG information on a strip chart recorder (not shown) and also provides a display of the pacemaker rate and pulse width information on a separate, typically digital display (not shown). The receiver 60 is intended for use in the physician's office, clinic or hospital, for the reception and analysis of EKG and stimulating pulse parameters of an implanted, artificial pacemaker.

With regard to FIG. 6A, the earpiece of the receiver telephone (not shown) is disposed adjacent a pick-up transducer 62, whereby the audio sound as produced thereby of a frequency corresponding to the amplitude of the patient's heart activity and the stimulating pulse, is converted to an electrical signal. The electrical signal output of the pick-up 62 is applied to a band-pass amplifier 64, which passes and amplifies only those audio frequencies of interest, typically in the range of 1000–2500 Hz. The band-pass amplifier output is applied to a high-pass amplifier 66, which further reduces unwanted, high-frequency signals. In turn, the high-pass amplifier output is applied to a high-gain amplifier 68 which further amplifies the signal to a usable level. The filtered and amplified signal output of the high-gain amplifier 68 is applied to a one-shot multiplier 70 which generates in response to the positive-going edge of the carrier signal a pulse of a predetermined, relatively short duration in the order of one-half the period of the carrier signal. The one-shot output is in turn applied to a driver 72 which increases the amplitude to a desired signal level in the order of ±8. OV.

The output of the driver 72 is applied to an EKG channel 80 and to an artifact channel 100. The EKG channel comprises a no-signal clamp 82 which "locks-off" the EKG channel in the absence of an input signal so that the output as derived therefrom and applied to its strip chart recorder is not noisy. The no-signal clamp output is applied in turn to a demodulator 84, which integrates the series of pulses applied to the EKG channel from the driver 72 to recover the original signal indicative of the patient's heart activity. The demodulated data is in turn applied to an EKG gate circuit 86, which blocks and prevents the stimulating pulses or pacemaker artifacts from distorting the EKG data to be displayed upon the strip chart recorder. During the time that a stimulating pulse is being received, the EKG gate circuit 86 is closed and an EKG level memory 88 stores the last EKG data signal received, to provide continuity before and after receipt of the stimulating pulse. Further, the EKG signal can be applied successively to a 60 Hz notch and a 2 Hz roll-off filter 90 to modify the frequency response of the receiver 60 at the option of the user. A switch (not shown) is provided on the front panel of the receiver 60 to permit the notch and roll-off filters 90 to be incorporated into or removed from the circuit of FIG. 6A.

Figure 4:
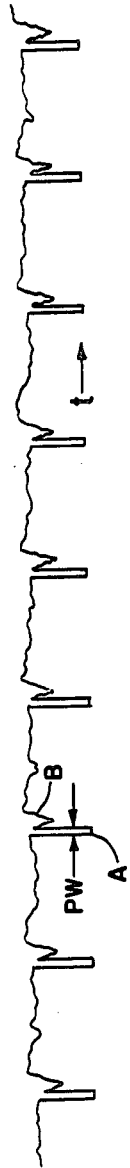
FIG. 4 is a graphical representation of the electrical activity of the patient and the heart pacemaker stimulating pulses inserted thereon, as transmitted and detected by the receiver in accordance with the teachings of this invention.

The pulsed outputs of the driver 72 are also applied to an artifact channel 100 comprising a filter 102, which removes unwanted high frequencies and produces a DC level proportional to the rate at which the train of input pulses are received. In turn, the DC level output of the filter 102 is applied to a high-pass filter 104 which produces a spike, when the DC level at its input changes abruptly. In turn, the spike outputs of high-pass filter 104, which correspond to the beginning and end of the multiplied stimulating pulse, are applied to an artifact detector circuit 106 taking the form of a flip-flop which sets at the leading edge of and resets at the trailing edge of the transmitted stimulating pulse, to generate a corresponding pulse. Such a flip-flop includes a threshold circuit rendering the circuit more sensitive to being reset than set. In this manner, in a marginal detection situation, the artifact detector 106 would thereby tend to reset, avoiding a "hang-up" condition. The output of the artifact detector 106 is applied to an artifact driver circuit 108, which serves to amplify these signals and to apply its amplified output to the artifact reinsertion amplifier 92, which recombines the amplified stimulating pulse signal and the EKG signal and applies the combined signals to a low-pass filter and driver circuit 96, which serves to remove the remnants of the carrier signal and to amplify the detected signals of interest. The filter and driver output is in turn applied to an output voltage divider 98, which properly scales the output for display, as shown in FIG. 4, on the strip chart recorder.

A calibrating generator 110 and a calibrating pulse driver 112 are used to calibrate the receiver and are not connected with the basic demodulating and display functions thereof.

The output of the artifact detector 106, as shown in FIG. 6A, is applied by conductor 107 to a leading and trailing edge trigger circuit 114 of a digital processing and display circuit as shown in FIG. 6B. Basically, the circuit of FIG. 6B employs a stable crystal oscillator 120 for providing a clock signal of a fixed frequency, e.g. 100 KHz, to a counter 124, whereby the pulse width and beats per minute (BPM) of the stimulating pulse are determined, for display upon a suitable digital display 128, such as one of light-emitting diodes. The leading and trailing edge trigger circuit 114 is responsive to the output of the artifact detector 106 to generate "clock" and "clear" command signals at both the beginning and end of each detected stimulating pulse. The trigger output is applied through a pulse-shaping and delay circuit 116 to a gang-type switch 118 comprised of sections 118a, 118b and 118c and disposable by operator manipulation in one of three modes or positions. In a first mode, corresponding to the switch position 1, the output of the pulse-shaping and delay circuit 116 is applied to up-down counters 124, and the output of the crystal oscillator 120 is applied to a divider 122, which applies a clock signal of a frequency to compensate for the multiplication provided by the transmitter 10, to the up terminal of the up-down counters 124. Since the stimulating pulse was originally multiplied by an illustrative factor of 40, increasing the counting frequency by a factor of 2.5 as determined by the oscillator 120 and the divider 122, to the up-down counters 124 gives a net multiplication of 100. In turn, the count indication as provided by the counters 124 is applied to latches 126 to be stored and to be subsequently displayed upon the digital, LED display 128. Illustratively, the decimal point may be placed upon the face of the LED display in a manner whereby the pulse width is given correctly in milliseconds.

Upon receipt of the trailing edge, the trigger circuit 114 applies both clock and clear commands by way of the pulse-shaping and delay circuit 116 to the up-down counters 124, to terminate the counting of the clock signal. Thus, the output derived from the up-down counters 124 corresponds, as indicated above, to the pulse width in milliseconds of the stimulating pulse. Because the counters 124 receive clock and clear commands at both the beginning and end of the stimulating pulse, both the pulse width and the pulse interval minus the pulse width are displayed. The pulse interval minus the pulse width is displayed for only the time between the leading and trailing edges of the pacemaker stimulating pulse and hence appears only as a flash upon the LED display 128, which in normal use does not detract from the subsequent display of the pulse width information after the occurrence of the trailing edge.

Further, as indicated in FIG. 6B, the switch 118 may be disposed to a second position, whereby the pulse signals generated by the trigger circuit 114 are applied by the switch 118 to the clear terminal of the up-down counters 124, while the output of the crystal oscillator 120, as divided by the divider 122 to provide a 1 KHz clock signal, is applied to the up terminal of the counters 124, whereby an output indicative of the interval between the stimulating pulses is provided to the LED display 128 in terms of milliseconds. In a third mode of operation, with the switch 118 disposed in its third position, a signal indicative of the leading edge as developed by the trigger circuit 114 is applied to a rate interpolation circuitry 117 which includes a read-only memory (ROM) that has been programmed with varying values of time intervals between the occurrences of the stimulating pulses. The divider circuit 122 provides a number of clocking pulses, e.g. 5, 2.5 and 5/16 KHz, whereby a wide range of time intervals may be accurately measured, e.g. the range of 30–150 msec. The clock signals are sequentially applied to the ROM to "step" the ROM through each of its storage locations until an output is derived from the pulse and shaping delay circuit 116 indicative of the occurrence of the next pulse stimulating signal, whereby the corresponding storage location of the ROM is applied through the switch section 118b to the up-down counters 124 to provide an indication of the interval between the stimulating pulses. The output of the counters 124 is in turn applied to the latches 126, whereby an indication of the interval is displayed upon the LED display 128.

Thus, there has been shown and described apparatus for detecting the pulse stimulating signals generated by an artificial cardiac pacemaker implanted within a patient and for transmitting corresponding signals stretched by a predetermined factor upon a relatively low bandwidth transmission medium to a distant station, whereat the signals may be received and detected to provide an accurate indication of the pulse widths. In this manner, an indication as to the state and to the further life expectancy of the power source of the artificial cardiac pacemaker may be determined with accuracy. Further, it is not then necessary for the patient to be physically present at the remote station, e.g. the doctor's office, clinic or hospital, and such checks of the power source may be made at regular intervals without inconvenience to the doctor or his patient. The predetermined multiplication factor is selected in view of the carrier frequency at which the pulse stimulator signal is transmitted over the low bandwidth medium.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. Apparatus for providing and transmitting together stimulating pulses as applied by an artificial pacemaker to a patient's heart and an electrocardiac signal of the patient's heart over a limited bandwidth medium to a remote station, said apparatus comprising:
    (a) modulation means for generating a carrier signal of a frequency to be transmitted over the limited bandwidth medium;
    (b) means for providing a multiplied signal of a pulse width corresponding to the pulse width between the leading and trailing edges of the stimulating pulse multiplied by a fixed factor;

(c) means for superimposing and applying the multiplied signal and the electrocardiac signal together to said modulation means, whereby the superimposed signals are transmitted over the limited bandwidth medium, the fixed factor selected to be not less than 30 and not more than 50 to insure that data of the multiplied signal is accurately transmitted over the limited bandwidth medium at the carrier frequency and does not obscure the electrocardiac signal; and (d) receiving apparatus for receiving the stimulating pulses as transmitted over the limited bandwidth medium and including display means for displaying an indication of the pulse width of the stimulating pulse, artifact detector means responsive to the transmitted signal for separating the stimulating pulse from other signals, means for detecting the leading and trailing edges of the separated stimulating pulse signal and for providing signals indicative thereof, clock means for providing clock pulses, and counter means responsive to the output of said detection means for counting the number of clock pulses occuring during the pulse width of the stimulating pulse to provide an output indicative thereof and display means responsive to the output of said counter means for providing display of the pulse width information.

2. The system as claimed in claim 1, wherein said receiving apparatus includes divider means responsive to the clock pulses of said clock means for applying clock pulses to said counter means at a rate whereby the count information displayed by said display means corresponds to the multiplied pulse width of the stimulating pulse.

* * * * *